US008613857B2

(12) United States Patent
Groeger et al.

(10) Patent No.: US 8,613,857 B2
(45) Date of Patent: Dec. 24, 2013

(54) PROCESSING OF REACTION SOLUTIONS FROM WHOLE-CELL BIOTRANSFORMATIONS

(75) Inventors: Harald Groeger, Hanau (DE); Claudia Rollmann, Alzenau (DE); Helge Werner, Bruchkoebel (DE); Francoise-Christine Chamouleau, L'Isle d'Espagnac (FR); Dittmar Orzewski, Dietzenbach (DE)

(73) Assignee: Evonik Degussa GmbH, Essen (DE)

( * ) Notice: Subject to any disclaimer, the term of this patent is extended or adjusted under 35 U.S.C. 154(b) by 303 days.

(21) Appl. No.: 11/766,189

(22) Filed: Jun. 21, 2007

(65) Prior Publication Data
US 2008/0006579 A1 Jan. 10, 2008

(30) Foreign Application Priority Data
Jun. 21, 2006 (DE) .................. 10 2006 028 817

(51) Int. Cl.
*B01D 15/00* (2006.01)
*C02F 1/44* (2006.01)

(52) U.S. Cl.
USPC ........... 210/639; 210/678; 210/749; 435/121; 435/128

(58) Field of Classification Search
USPC ................ 210/678, 639, 749; 435/121, 128
See application file for complete search history.

(56) References Cited

U.S. PATENT DOCUMENTS

| 4,000,066 | A | * | 12/1976 | Squires | 210/678 |
| 4,288,552 | A | * | 9/1981 | Gestrelius | 435/174 |
| 5,858,736 | A | * | 1/1999 | Di Cosimo et al. | 435/121 |
| 2005/0009154 | A1 | * | 1/2005 | Wong et al. | 435/128 |
| 2006/0216801 | A1 | | 9/2006 | Groger et al. | |
| 2006/0246561 | A1 | | 11/2006 | Hummel et al. | |
| 2007/0020741 | A1 | | 1/2007 | Drauz et al. | |
| 2007/0149781 | A1 | | 6/2007 | Riermeier et al. | |
| 2008/0145904 | A1 | * | 6/2008 | Groger et al. | 435/157 |

FOREIGN PATENT DOCUMENTS

| DE | 102004043748 | | 3/2006 | |
| JP | 62-205787 | | 9/1987 | |
| WO | WO2005/121350 | * | 9/2005 | 435/128 |
| WO | WO 2006015802 A2 | * | 2/2006 | |
| WO | WO 2006/027081 | | 3/2006 | |
| WO | WO2008/003565 | * | 10/2008 | 210/639 |

OTHER PUBLICATIONS

Groeger et al., Enantioselective Reduction of Ketones with "Designer Cells" at High Substrate Concentrations: Highly Efficient Access to Functionalized Optically Active Alcohols, Jul. 21, 2006, Angewandte Chemie, 2006-45, pp. 5677-5681.*
Daniel R. Yazbeck, et al., "Challenges in the development of an efficient enzymatic process in the pharmaceutical industry", Tetrahedron: Asymmetry, vol. 15, No. 18, XP-004575045, Sep. 20, 2004, pp. 2757-2763.
U.S. Appl. No. 11/629,407, filed Dec. 13, 2006, Groeger, et al.
U.S. Appl. No. 11/766,164, filed Jun. 21, 2007, Groeger, et al.
U.S. Appl. No. 10/593,119, filed Mar. 10, 2005, Schulze, et al.
German translation of Japanese Office Action in Patent Application No. 2007-164177 dated Feb. 6, 2013.

* cited by examiner

*Primary Examiner* — Dirk Bass
(74) *Attorney, Agent, or Firm* — Oblon, Spivak, McClelland, Maier & Neustadt, L.L.P.

(57) ABSTRACT

A product is enriched by a method for the processing of a reaction solution, in which: a) a pH value of the reaction solution is adjusted to less than 4; wherein said reaction solution comprises a whole-cell catalyst, an aqueous component, and an organic component, wherein the organic component contains a product to be enriched; and b) the reaction solution is filtered in the presence of a filter aid, thereby enriching the product.

21 Claims, No Drawings

PROCESSING OF REACTION SOLUTIONS FROM WHOLE-CELL BIOTRANSFORMATIONS

BACKGROUND OF THE INVENTION

1. Field of the Invention

The present invention relates to a method for processing of reaction solutions, containing whole-cell catalysts, an aqueous component and an organic component, wherein the organic component contains the product to be enriched.

2. Description of the Related Art

Biotransformations with whole-cell catalysts (among other things, also called whole-cell biocatalysts) have proved to be highly attractive production techniques for the synthesis of fine chemicals (for a survey, see e.g.: S. Buchholz, H. Gröger, "Ganzzellbiokatalyse" in: Angewandte Mikrobiologie, Chapter 8, Springer-Verlag, Berlin, 2006, p. 161f). In comparison with isolated, especially purified enzymes, recombinant whole-cell catalysts often represent a more cost-effective type of catalyst, since processing and purification steps are omitted in the production of the whole-cell catalyst by the direct use of the biomass obtained in fermentation (in contrast to the use of isolated enzymes). Furthermore, the use of whole-cell catalysts in redox reactions permits the reactions to be carried out without addition of external amounts of expensive cofactor (see WO/2005/121350), whereas addition of a cofactor is necessary in reactions with isolated enzymes.

At present various methods are known for the processing of biotransformation reaction solutions containing whole-cell catalysts. A general problem is the formation of emulsions in the extraction operation, together with very long, economically unacceptable processing times, especially extraction and/or filtration times, of for example several hours even at the laboratory scale or even impossibility of separating such mixtures, especially as a result of formation of stable emulsions. The work of G. Jörg, K. Leppchen, T. Daussmann, M. Bertau, Chem. Ing. Techn. 2004, 76, 1739-1742 may be cited as a typical example of this, according to which the chief complication in extractive processing of the whole-cell biotransformation with high cell density is the formation of stable gels and slimes in contact with the organic solvent. The corresponding consequence of this is the need for subsequent purification of the product by distillation, and large losses of yield in downstream processing, accompanied by reduced overall economy of the process and high production costs.

Furthermore, in a survey from the year 2004 on downstream processing of biotransformation solutions, Yazbeck et al. (D. R. Yazbeck, C. A. Martinez, S. Hu, J. Tao, Tetrahedron: Asymmetry 2004, 15, 2757-2763) refer in detail to the often complicated product isolation as a result of the formation of emulsions. It is pointed out that not many user-friendly technologies are available for avoiding this problem, and there is an increasing demand for better ways of improving downstream processing in such systems.

Accordingly, generally there is considerable interest in processing methods that lead to avoidance of the aforementioned limitations. To date, the following methods have been developed:

In the whole-cell-catalyzed synthesis of 2-phenylethanol, in order to avoid the formation of emulsions, which even occurs at low substrate—or product concentrations of <10 g/L, Serp et al. use synthetic resin immobilizates, in which an organic solvent (dibutyl sebacate) is enclosed, for the extraction (D. Serp, U. von Stockar, I. W. Marison, Biotechnol. Bioeng. 2003, 82, 103-110). The product 2-phenylethanol is removed in situ from the reaction medium by being absorbed in the synthetic resin immobilizates. However, this method using organic solvents enclosed in immobilizates is very expensive and cost-intensive. Moreover, the product concentrations used in the solutions are low (<10 g/L).

Another method for processing emulsions consisting of an organic phase, aqueous phase and whole-cell catalysts uses several hydrocyclones arranged in series (L.-Q. Yu, T. A. Meyer, B. R. Folsom, E P 900 113, 1999). The overflow from one hydrocyclone is always transferred to the next hydrocyclone, so that the aqueous phase can be separated from the organic phase and the biocatalyst. However, this method requires high capital expenditure and is correspondingly expensive.

Recently, Bertau et al. showed that it is possible to avoid stable gels and slimes in contact with the organic solvent by using suitable enzymes as demulsifiers (G. Jörg, K. Leppchen, T. Daussmann, M. Bertau, Chem. Ing. Techn. 2004, 76, 1739-1742 and G. Jörg, K. Leppchen, T. Daussmann, M. Bertau, Biotechnol. Bioeng. 2004, 87, 525-536). In this case the problem of gel formation could be suppressed by bioemulsifiers derived from the whole-cell catalyst, which are released by the microorganisms into the medium. A disadvantage, however, is the need for a further, additional enzymatic component, especially if this is only available at great expense. Another problem is the occurrence of side reactions, caused by the proteases that are added (G. Jörg, K. Leppchen, T. Daussmann, M. Bertau, Chem. Ing. Techn. 2004, 76, 1739-1742). There is preferably cleavage of e.g. ester groups, but also of amide groups.

As an alternative, the use of a filter aid after biotransformation has been carried out is reported by Hanson et al. (R. L. Hanson, S. Goldberg, A. Goswami, T. P. Tully, R. N. Patel, Adv. Synth. Catal. 2005, 347, 1073-1080). According to this method, reduction of an organic ketone substrate is carried out with a whole-cell catalyst at a neutral pH (pH 7) and an amount of substrate of about 20 g/L of reaction volume using the high-priced filter aid AMBERLITE XAD-16 in a 10-fold amount relative to the amount of organic substrate used. Although the use of AMBERLITE XAD-16 proved suitable, direct extraction with ethyl-ethyl acetate or MTBE in the absence of such a filter aid did not prove practicable and led to emulsion problems. Drawbacks of the method of Hanson et al. are, however, limitations such as the high consumption of high-priced AMBERLITE XAD-16 as filter aid at a factor of 10 relative to the organic component, even at a low proportion of organic ketone substrate of only about 20 g/L.

SUMMARY OF THE INVENTION

An object of the present invention was therefore to provide a quick, simple, inexpensive and effective method for the processing of reaction solutions resulting from whole-cell biotransformations, said method being based moreover on reasonably-priced solvents or additives and requiring little capital expenditure.

A particular problem was to provide a method for processing a reaction solution containing whole-cell catalysts, an aqueous component and an organic component with a proportion of >50 g/L of the total volume, avoiding the aforementioned disadvantages of the related art. In particular, the method was to be suitable for the processing of reaction solutions resulting from redox reactions with whole-cell catalysts, where the organic component consists to >90% (w/w) of an enantiomerically enriched alcohol.

This and other objects have been achieved by the present invention the first embodiment of which includes a method for the processing of a reaction solution, comprising:

a) adjusting a pH value of said reaction solution to less than 4;
   wherein said reaction solution comprises a whole-cell catalyst, an aqueous component, and an organic component,
   wherein the organic component contains a product to be enriched; and
b) filtration of the reaction solution in the presence of a filter aid, thereby enriching said product.

DETAILED DESCRIPTION OF THE INVENTION

The present invention relates to a method for processing of reaction solutions, containing whole-cell catalysts, an aqueous component and an organic component, wherein the organic component contains the product to be enriched. The present invention relates in particular to a method for the processing of reaction solutions resulting from whole-cell biotransformations, containing whole-cell catalysts, an aqueous component and an organic component with a proportion of >50 g/L of the total volume.

The object of the present invention is solved by a method for the processing of reaction solutions, containing whole-cell catalysts, an aqueous component and an organic component, wherein the organic component contains the product to be enriched, with the following steps:
a) adjustment of the pH value to less than 4;
b) filtration of the reaction solution in the presence of a filter aid, preferably in the reaction solution;
c) optionally: further enrichment and/or purification of the product contained in the organic component.

The pH in step a) includes all values and subvalues therebetween, especially including 0.5, 1, 1.5, 2, 2.5, 3 and 3.5.

Surprisingly it was found that by lowering the pH value of the reaction solution to less than 4, the filtration rate of the reaction solution is increased enormously, if filtration is additionally carried out in the presence of a filter aid. In particular, this is also surprising because with both lowering of the pH value alone (Example 4=comparative example), and filtration in the presence of a filter aid without lowering the pH (Examples 2, 3=comparative examples) there is unsatisfactory product separation/product processing starting from the emulsion that forms in the whole-cell-catalyzed reaction. In this case the filter aid is preferably present in the reaction solution. Therefore, it is preferably added to the reaction mixture prior to filtration (before or after adjustment of the pH value to less than pH 4), as shown for example in Example 6 according to the present invention. Alternatively, however—after adjustment of the pH value of the reaction mixture to pH below 4—the reaction mixture can be filtered using a filter charged with the filter aid (see e.g. Example 5).

The present invention thus provides a quick, simple, inexpensive and effective method, based on reasonably-priced solvents or additives, for the processing of reaction solutions resulting from whole-cell biotransformations, requiring only low capital expenditure. The method according to the present invention is suitable in particular for processing a reaction solution containing whole-cell catalysts, an aqueous component and an organic component with a proportion of >50 g/L of the total volume, and especially for the processing of reaction solutions resulting from redox reactions with whole-cell catalysts, where the organic component consists to more than 90% (w/w) of an enantiomerically enriched alcohol. The amount of enantiomerically enriched alcohol of the organic component includes all values and subvalues therebetween, especially including 91, 92, 93, 94, 95, 96, 97, 98, 99, 99.5 and 100% (w/w).

Furthermore, a preferred method has the following steps:
b1) washing of the filter cake obtained during filtration with an organic solvent or a mixture of organic solvents;
b2) optionally: extraction of the aqueous component of the filtrate obtained in step a) with the filtrate obtained in step b1) or a newly added organic solvent or a mixture of organic solvents; and
b3) removal of the organic solvent from the organic component.

The organic component in the reaction solution to be processed is understood to be the desired end product of a reaction, possibly mixed with the corresponding starting product and/or any by-products that are formed, the end product being for example an optically active alcohol, which is obtained from a corresponding ketone after a reaction catalyzed by the whole-cell catalysts. As a rule, after the reaction the desired end product is present in the organic component as a mixture with the starting product, for example at a ratio of 95%:5% (w/w), 97%:3% (w/w) or higher. The ratio of end product to the starting product includes all values and subvalues therebetween, especially including 95.5:4.5, 96:4, 96.5:3.5, 97:3, 97.5:2.5, 98:2, 98.5:1.5, 99:1, 99.5:0.5 and 100:0 (w/w).

Furthermore, a method is preferred in which the organic component consists to more than 90% (w/w), and especially preferably to more than 95% (w/w) of an optically active alcohol. The amount of optically active alcohol of the organic component includes all values and subvalues therebetween, especially including 91, 92, 93, 94, 95, 96, 97, 98, 99, 99.5 and 100% (w/w).

In particular, the method according to the present invention overcomes the problems of the related art in product separation from reaction solutions to be processed, which comprise an emulsion of whole-cell catalysts, an aqueous component and an organic component containing the product to be enriched.

It is further preferred for the whole-cell catalysts in the reaction solution to represent a proportion of up to 75 g/L, preferably up to 50 g/L, especially preferably up to 30 g/L and quite especially preferably up to 25 g/L (g relative to the wet weight of the biomass). The amount of whole cell catalyst in the reaction solution includes all values and subvalues therebetween, especially including 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70 g/l. In that case a proportion of whole-cell catalysts in the reaction solution of at least 10 g/L, and especially of at least 20 g/L (g relative to the wet weight of the biomass) is especially preferred.

All known filter aids can be used as the filter aids. In another preferred method, the filter aid is selected from the group comprising cellulose, silica gel, kieselguhr, perlite, cristobalite, filter quartz gravel, activated carbon, charcoal, wood flour, filter aids based on synthetic resin and mixtures thereof. The use of kieselguhr, cristobalite and filter quartz gravel and mixtures of these components as filter aid is especially preferred. Quite especially preferably, the filter aid with the product designation Celite Hyflo Supercel as trade name is used.

In a preferred embodiment of the method according to the invention, the reaction solution is adjusted to a pH value of pH less than 3, preferably pH 2 to 3, and especially preferably pH 2.5 to 3.

In further variants of the method, MTBE (methyl tert-butyl ether) and/or ETBE (ethyl tert-butyl ether) and/or ethyl acetate are used as organic solvent for washing the filter cake and/or extraction of the aqueous component.

In a preferred method, the proportion of the organic component is greater than 50 g/L, preferably greater than 100 g/L, of the total volume of the reaction solution.

Having generally described this invention, a further understanding can be obtained by reference to certain specific examples which are provided herein for purposes of illustration only, and are not intended to be limiting unless otherwise specified.

EXAMPLES

General Explanation of the Experimental Examples

The following tests were carried out in order to solve the problems of the state of the art:

The following test represents a comparative example: following the method of Hanson et al. (Adv. Synth. Catal. 2005, 347, 1073-1080), a filter aid was used after carrying out biotransformation. Instead of the AMBERLITE XAD-16 used by Hanson et al., the more attractively priced filter aid Celite Hyflo Supercel (=trade name) was used. However, this method proved to be unsuitable for application to biotransformations with a proportion of an organic component greater than 50 g/L (Example 2=comparative example). After carrying out the biotransformations in the neutral pH-range (pH 6.5-7.0), a stable emulsion formed, which could not be processed in a practicable manner using a filter aid (in the form of a layer of Celite on the filter) and led to very slow filtration with a filtration time of 6.5 hours, and moreover the subsequent phase separation in the extraction operation was also very slow, taking more than 5 hours. Furthermore, the isolation yield achieved was a low 20.1%.

A similarly unsatisfactory, long filtration time of 7 hours was observed if the filter aid Celite Hyflo Supercel was stirred into the reaction solution with a pH value of 6.5 to 7 and then the mixture was filtered (Example 3=comparative example). The isolation yield achieved was again unsatisfactory, at 55.4%.

Furthermore, a corresponding test without using a filter aid even with lowering of pH to 4 did not provide significant filtration, so that in this case filtration had to be interrupted (Example 4=comparative example).

In contrast, when processing is carried out by the method according to the invention, short filtration times were achieved, together with high isolation yields (Examples 5 and 6). For example, an isolation yield of 79.2% was obtained if the pH value after completion of biotransformation was first adjusted to pH 2.4, the resultant reaction mixture was filtered through a filter charged with an approx. 0.5 cm layer of Celite (Celite Hyflo Supercel) and was then washed with an organic solvent and the aqueous phase was additionally submitted to extractive processing (Example 5). In this method, moreover, a short filtration time of less than 5 minutes was achieved.

A high isolation yield (78.4%) was also obtained if the pH value after biotransformation was adjusted to pH 2.6, Celite Hyflo Supercel was added to the reaction mixture and it was then filtered, the filter cake washed with an organic solvent and the aqueous phase was submitted to extractive processing (Example 6). In this Example 6, once again a short filtration time of less than 5 minutes was achieved.

EXPERIMENTAL EXAMPLES

Example 1

General Test Specification for Preparation of the Reaction Mixture for the Processing Tests; 500 mM Substrate Concentration In a Titrino reaction vessel (manufacturer: Metrohm), the whole-cell catalyst E. coli DSM14459 (pNO5c, pNO8c) described in WO/2005/121350, containing an (R)-alcohol dehydrogenase from *Lactobacillus kefir* and a glucose dehydrogenase from *Thermoplasma acidophilum*, corresponding to a biomass concentration of approx. 50 g/L (Examples 2 and 3) or approx. 25 g/L (Examples 4 to 6), D-glucose (1.05 to 6 equivalents relative to the amount of p-chloroacetophenone used) and 3.87 g p-chloroacetophenone (corresponding to a substrate concentration of 0.5 M relative to the volume of phosphate buffer used) were added to 50 mL of a phosphate buffer (0.1M, adjusted to pH 7.0) at room temperature. The reaction mixture was stirred at room temperature for 22 h, keeping the pH constant in a pH-range of pH 6.5 to 7.0 by adding sodium hydroxide solution (2M NaOH). Samples were taken at regular intervals and the degree of conversion was determined by HPLC. After a reaction time of 22 h, the degree of conversion to the product (R)-(4-chlorophenyl)ethan-1-ol was greater than 99%. The reaction mixture was then used for the processing tests.

Example 2

Comparative Example

The reaction solution (emulsion) prepared by the method described in Example 1 (double batch size) was filtered through a Schott glass filter with a pore size of 40 to 200 μm, charged with an approx. 0.5 cm thick layer of Celite (Celite Hyflo Supercel), with application of a vacuum. A filtration time of 6.5 hours was required. The—very turbid—filtrate was extracted with 3×50 mL MTBE, leading to formation of a mixed phase, causing very slow separation taking more than 5 hours. After drying the combined organic phases over magnesium sulfate, filtration and then removal of the organic solvent in vacuum (50° C., water-jet vacuum) the desired product was obtained at an isolation yield of 20.1%.

Example 3

Comparative Example 100 mL MTBE and 1.5 g Celite (Celite Hyflo Supercel) were added to the reaction solution (emulsion) prepared by the method described in Example 1. After stirring for 5 minutes, it was filtered under vacuum. A filtration time of 7 hours was required. Then the filter cake washed with 50 mL MTBE. The wash solution was added to the—very turbid—filtrate and the resultant mixture was extracted with 2×50 mL MTBE. After drying the combined organic phases over magnesium sulfate, filtration and then removal of the organic solvent in vacuum (50° C., water-jet vacuum) the desired product was obtained at an isolation yield of 55.4%.

Example 4

Comparative Example

Concentrated hydrochloric acid was added to the reaction solution (emulsion) prepared by the method described in Example 1 (0.6 times batch size) until the pH value was adjusted to pH 4.0, when flocculation of the biomass occurs. Then it was filtered under vacuum, but no notable filtration occurred owing to gel formation, and accordingly filtration was interrupted.

Example 5

Example According to the Invention

Concentrated hydrochloric acid was added to the reaction solution (emulsion) prepared by the method described in Example 1 (0.6 times batch size) until the pH value was adjusted to pH 2.4, when flocculation of the biomass occurs. Then it was filtered under vacuum through a filter that was charged with an approx. 0.5 cm layer of Celite (Celite Hyflo Supercel), observing very rapid filtration taking less than 5 minutes. Then the filter cake was washed with 30 mL MTBE and a further 45 mL was added to the turbid filtrate. There was good phase separation. After further extraction with 75 mL MTBE the combined organic phases were dried over magnesium sulfate, filtered and then the organic solvent was removed under vacuum (50° C., water-jet vacuum), and the desired product was obtained at an isolation yield of 79.2%.

Example 6

Example According to the Invention

Concentrated hydrochloric acid was added to the reaction solution (emulsion) prepared by the method described in Example 1 until the pH value was adjusted to pH 2.6, when flocculation of the biomass occurs, and 2 g Celite (Celite Hyflo Supercel) was added. Then it was filtered under vacuum, observing good filtration taking less than 5 minutes. Then the filter cake washed with 2×80 mL MTBE and the (aqueous, first) filtrate was washed with the two organic washing phases (2×80 mL), in each case observing good phase separation. The combined organic phases were dried over magnesium sulfate, filtered and then the organic solvent was removed under vacuum (50° C., water-jet vacuum), and the desired product was obtained at an isolation yield of 78.4%. The enantiomeric excess of the product formed was greater than 99.8% ee.

German patent application 102006028817.3 filed Jun. 21, 2006, is incorporated herein by reference.

Numerous modifications and variations on the present invention were possible in light of the above teachings. It is therefore to be understood that within the scope of the appended claims, the invention may be practiced otherwise than as specifically described herein.

The invention claimed is:

1. A method for the processing of a reaction solution, comprising:
   a) first, adjusting a pH value of said reaction solution to less than 4;
      wherein said reaction solution comprises a whole-cell catalyst, an aqueous component, and an organic component,
      wherein the organic component contains a product to be enriched; and
   b) subsequently, filtration of the reaction solution in the presence of a filter aid, to obtain an organic phase in the filtrate which contains the product, thereby enriching said product.

2. The method as claimed in claim 1, further comprising:
   b1) washing of a filter cake obtained during said filtration with an organic solvent or a mixture of organic solvents;
   b2) optionally, extraction of the aqueous component of the filtrate obtained in step a) with the filtrate obtained in step b1) or a newly added organic solvent or a mixture of organic solvents; and
   b3) removal of the organic solvent or mixture of organic solvents from the organic component.

3. The method as claimed in claim 1, wherein the organic component comprises more than 90% (w/w) of an optically active alcohol.

4. The method as claimed in claim 1, wherein the reaction solution to be processed is an emulsion of whole-cell catalysts, an aqueous component and an organic component containing the product to be enriched.

5. The method as claimed in claim 1, wherein the whole-cell catalyst in the reaction solution represents a proportion of up to 75 g/L (g relative to the wet weight of the biomass).

6. The method as claimed in claim 1, wherein a filter aid is used, selected from the group consisting of cellulose, silica gel, kieselguhr, perlite, activated carbon, charcoal, wood flour, filter aids based on synthetic resin and mixtures thereof.

7. The method as claimed in claim 1, wherein kieselguhr, cristobalite and filter quartz gravel and mixtures of these components are used as filter aid.

8. The method as claimed in claim 1, wherein the reaction solution is adjusted to a pH value of pH below 3.

9. The method as claimed in claim 1, wherein MTBE (methyl tert-butyl ether) and/or ETBE (ethyl tert-butyl ether) and/or ethyl acetate are used as organic solvent for washing the filter cake and/or extracting an aqueous component.

10. The method as claimed in claim 1, wherein an organic fraction represents a proportion of more than 50 g/L.

11. The method as claimed in claim 1, comprising:
   c) enrichment and/or purification of the product contained in the organic component.

12. The method as claimed in claim 2, wherein step b2) is carried out.

13. The method as claimed in claim 2, wherein step b2) is carried out and is extraction of the aqueous component of the filtrate obtained in step a) with the filtrate obtained in step b1).

14. The method as claimed in claim 2, wherein step b2) is carried out and is extraction of the aqueous component of the filtrate obtained in step a) with a newly added organic solvent or a mixture of organic solvents.

15. The method as claimed in claim 1, wherein the whole-cell catalyst in the reaction solution represents a proportion of up to 50 g/L (g relative to the wet weight of the biomass).

16. The method as claimed in claim 1, wherein the whole-cell catalyst in the reaction solution represents a proportion of up to 30 g/L (g relative to the wet weight of the biomass).

17. The method as claimed in claim 1, wherein the whole-cell catalyst in the reaction solution represents a proportion of up to 25 g/L (g relative to the wet weight of the biomass).

18. The method as claimed in claim 1, wherein the reaction solution is adjusted to a pH value of pH 2 to 3.

19. The method as claimed in claim 1, wherein the reaction solution is adjusted to a pH value of pH 2.5 to 3.

20. The method as claimed in claim 1, wherein an organic fraction represents a proportion of more than 100 g/L, of the total volume of the reaction solution.

21. The method as claimed in claim 1, wherein said organic component comprises at least 90% (w/w) of an enantiomerically enriched alcohol.

* * * * *

UNITED STATES PATENT AND TRADEMARK OFFICE
CERTIFICATE OF CORRECTION

| | | |
|---|---|---|
| PATENT NO. | : 8,613,857 B2 | Page 1 of 1 |
| APPLICATION NO. | : 11/766189 | |
| DATED | : December 24, 2013 | |
| INVENTOR(S) | : Harald Groeger et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 986 days.

Signed and Sealed this
Twenty-first Day of July, 2015

Michelle K. Lee
*Director of the United States Patent and Trademark Office*